US00PP31706P2

(12) United States Plant Patent

Malinowski et al.

(10) Patent No.: US PP31,706 P2
(45) Date of Patent: Apr. 28, 2020

(54) *HIBISCUS* PLANT NAMED '15334-1 GR'

(50) Latin Name: ***Hibiscus* hybrid (L.)**
Varietal Denomination: 15334-1 GR

(71) Applicant: The Texas A&M University System, College Station, TX (US)

(72) Inventors: Dariusz P. Malinowski, Vernon, TX (US); William E. Pinchak, Vernon, TX (US); R. Steve Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/501,697

(22) Filed: May 22, 2019

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
See application file for complete search history.

(56) References Cited

U.S. PATENT DOCUMENTS

PP27,838 P2 4/2017 Hansen

OTHER PUBLICATIONS

U.S. Appl. No. 16/501,691, filed May 22, 2019, Malinowski et al.
U.S. Appl. No. 16/501,698, filed May 22, 2019, Malinowski et al.
U.S. Appl. No. 16/501,696, filed May 22, 2019, Malinowski et al.
U.S. Appl. No. 16/501,693, filed May 22, 2019, Malinowski et al.
U.S. Appl. No. 16/501,695, filed May 22, 2019, Malinowski et al.
U.S. Appl. No. 16/501,692, filed May 22, 2019, Malinowski et al.
U.S. Appl. No. 16/501,694, filed May 22, 2019, Malinowski et al.

*Primary Examiner* — Annette H Para
(74) *Attorney, Agent, or Firm* — Dentons US LLP

(57) ABSTRACT

'15334-1 GR' is a new and distinct hardy herbaceous *Hibiscus* hybrid with novel characteristics that include upright branched stems, numerous, outward-facing, flowers with a background between strong red and deep purplish pink and a strong red eye zone, a prolonged blooming season, and generally hastate, trilobed leaves with slightly indented margins.

5 Drawing Sheets

Latin name of the genus and species of the plant claimed: *Hibiscus* hybrid (L.).

Cultivar denomination: '15334-1 GR'.

BACKGROUND OF THE INVENTION

The invention relates to the new and distinct *hibiscus* plant '15334-1 GR'. '15334-1 GR' was generated from a cross performed on Jul. 10, 2014 near Vernon, Tex. between '11274-5' (pod parent, unpatented) and '13056-2' (pollen parent, unpatented). The pedigrees of each parent reflect a complex mixture of *hibiscus* species that include, for example, *H. mocheutos, H. coccineus*, or *H. militaris*. The seed from this cross was harvested on Aug. 24, 2014 and the '15334-1 GR' seedling was selected in the summer of 2015. '15334-1 GR' was first asexually propagated near Vernon, Tex. in 2016 by stem tip cuttings. The resulting as well as subsequent asexually propagated plants have been stable and true to type throughout successive generations.

SUMMARY OF THE INVENTION

'15334-1 GR' differs from its parents and all other known hardy herbaceous *hibiscus* plants. The following are the most outstanding and distinguishing characteristics of '15334-1 GR': (1) it is a hardy perennial with dense branching and a compact growth habit; (2) it blooms profusely over a prolonged season; and (3) its flowers exhibit a background between strong red (RHS 53C) and deep purplish pink (RHS 55A) and a strong red (RHS 53B) eye zone.

'15334-1 GR' plants can be readily and unambiguously distinguished from those of its parents. '15334-1 GR' plants exhibit flowers that are between strong red (RHS 53C) and deep purplish pink (RHS 55A) and that have an average diameter of 23 cm and generally hastate leaves with slightly indented margins. Whereas, '11274-5' plants (pod parent) exhibit deep purplish pink (RHS 55A) flowers that have an average diameter of 20 cm and hastate leaves with deeply indented margins; and '13056-2' plants (pollen parent) exhibit strong purplish pink (RHS 55B) flowers that have an average diameter of 30 cm and ovate leaves with indented margins.

'Mars Madness' (U.S. Plant Pat. No. 27,838) is the *hibiscus* plant that exhibits flowers with a shape that is most similar to those of '15334-1 GR'. Nonetheless, plants of '15334-1 GR' and 'Mars Madness' can also be readily and unambiguously distinguished from one another at least based upon petal shape and foliage color. 'Mars Madness' plants exhibit ribbed petals with smooth margins and dark-green (RHS 137A) and greyed-purple (between RHS 187A and RHS N137A) foliage; whereas, '15334-1 GR' plants exhibit ribbed petals with slightly frilled margins and moderate yellowish green (between RHS 137D and RHS 138A) foliage.

BRIEF DESCRIPTION OF THE DRAWINGS

'15334-1 GR' is illustrated by the accompanying photographs, which show the plant's form, foliage, flowers, and leaves. The colors shown are as true as can be reasonably obtained by conventional photographic procedures.

DETAILED BOTANICAL DESCRIPTION

Figure 1:
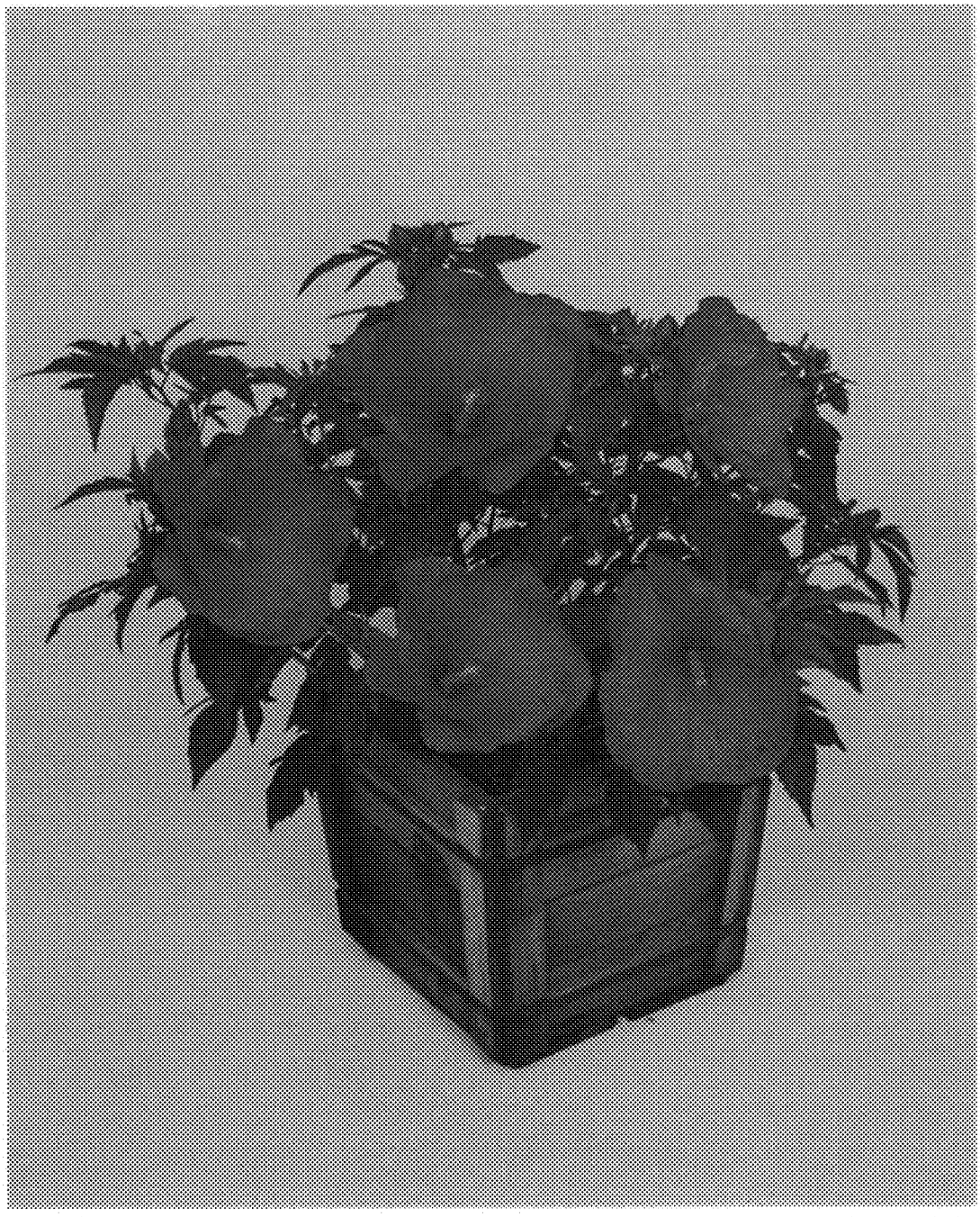
FIG. 1—Shows a 6-week-old '15334-1 GR' plant in a container.
Figure 2:
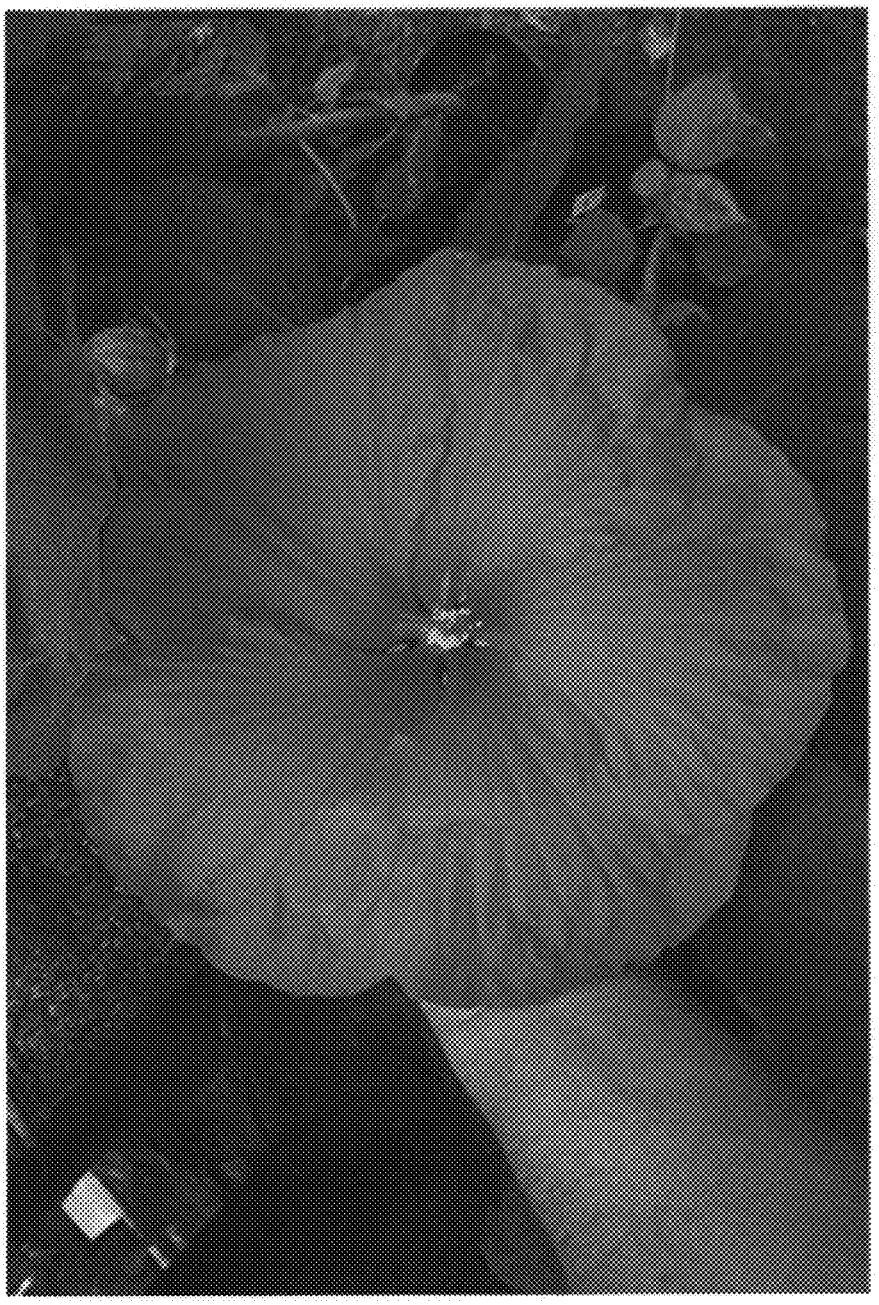
FIG. 2—Shows a '15334-1 GR' flower as seen looking directly at the adaxial surface of the petals on a 2-year old plant.
Figure 3:
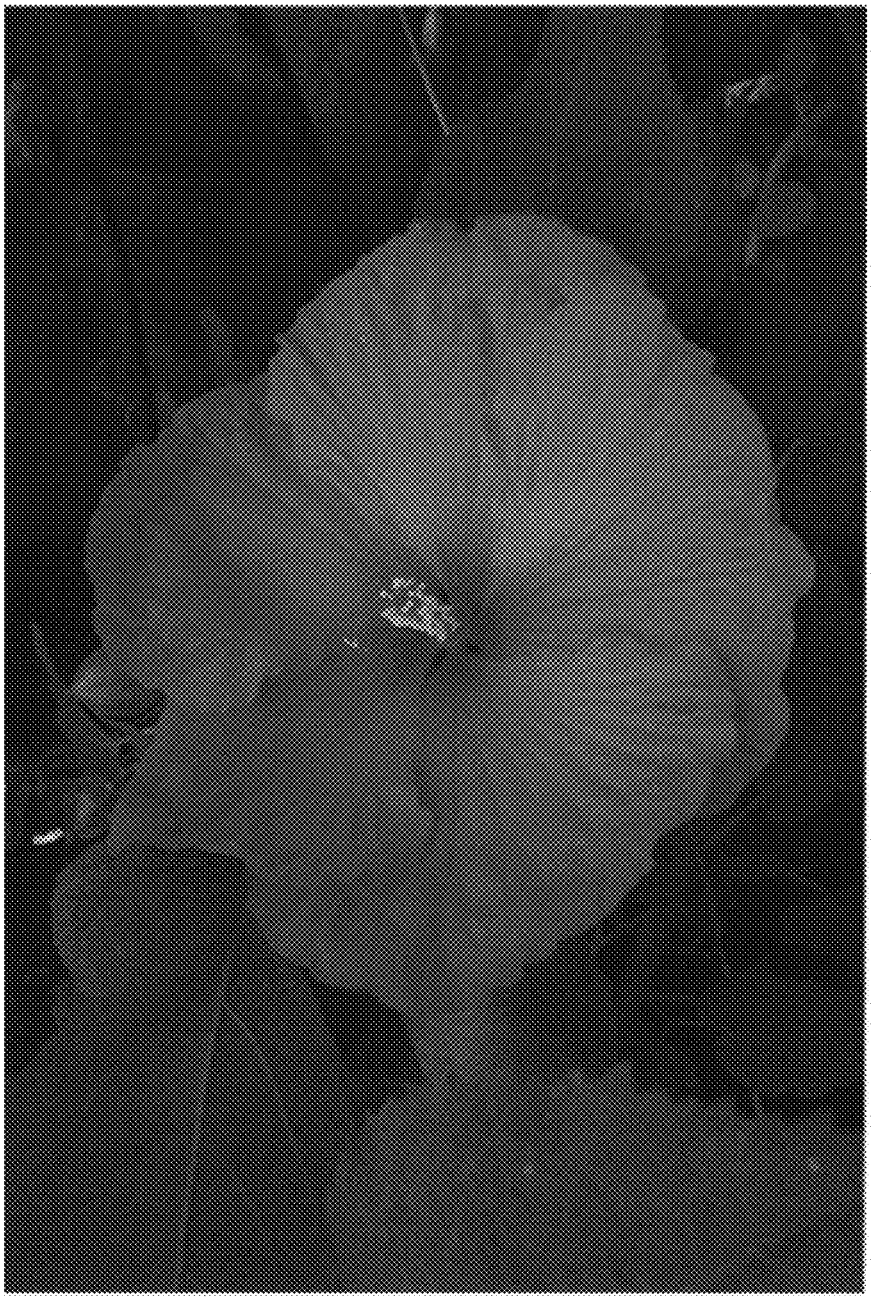
FIG. 3—Shows a '15334-1 GR' flower as seen looking slightly askew from the adaxial surface of the petals on a 2-year old plant.
Figure 4:
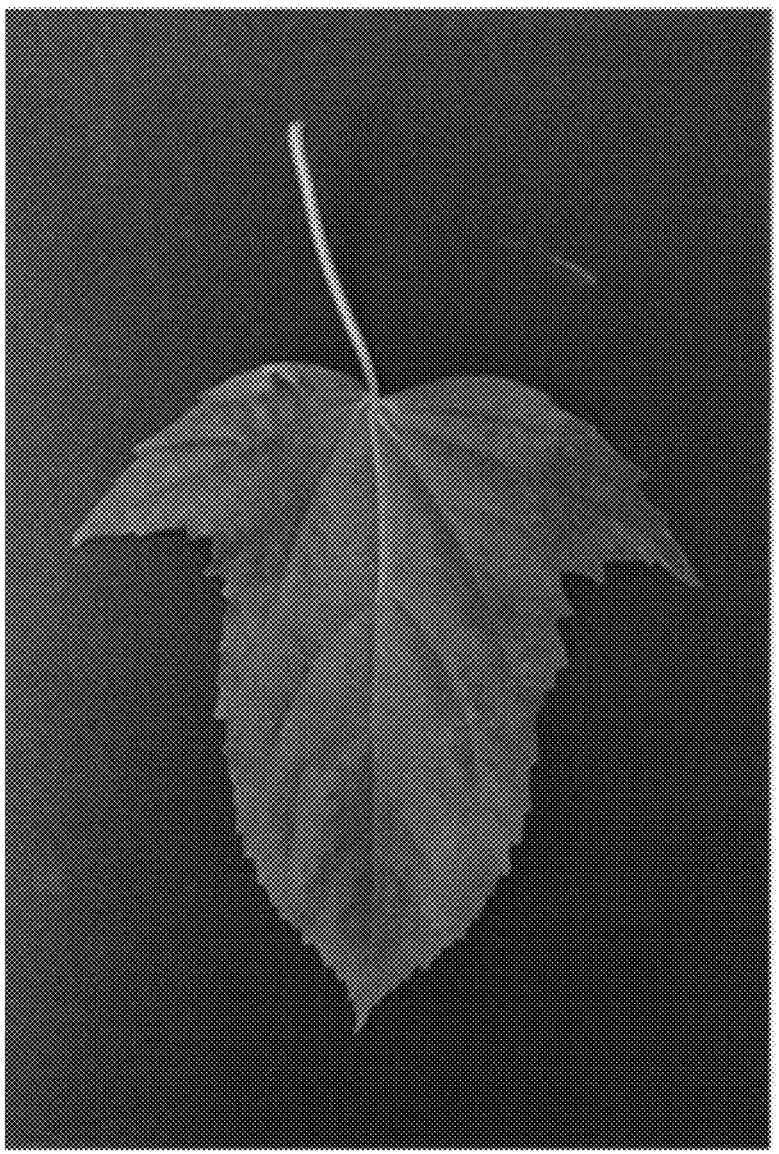
FIG. 4—Shows a '15334-1 GR' leaf that is representative of one of the two most common shapes.
Figure 5:
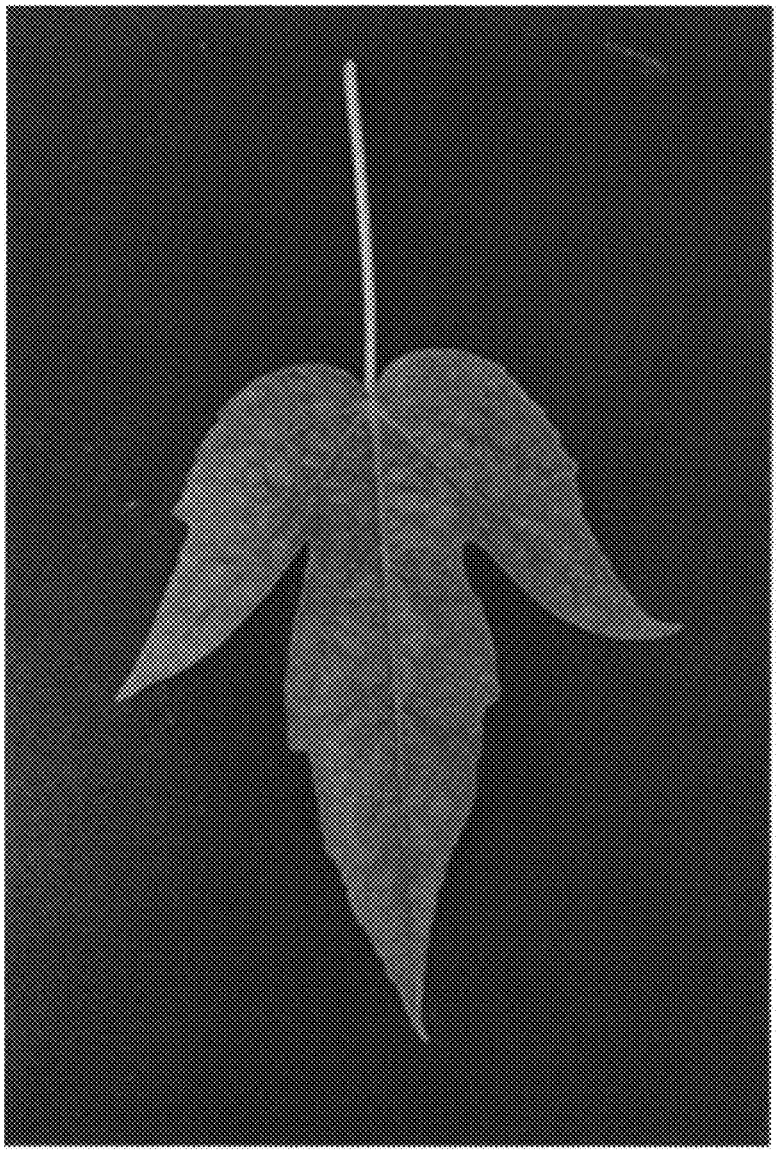
FIG. 5—Shows a '15334-1 GR' leaf that is representative of one of the two most common shapes.

The following detailed description sets forth the distinctive characteristics of '15334-1 GR'. The detailed description was obtained using two-year-old plants grown in loamy sand, open-field, full sun trials at a nursery near Vernon, Tex., during which the plants were supplemented with fertilizer and water as needed. These plants are natural habit and were not treated with plant growth regulators and they were not pinched at any time in the growth year. '15334-1 GR' has not been observed under all possible environments, and certain characteristics may vary slightly under different environmental conditions. Color references are to The Royal Horticultural Society Colour Chart of The Royal Horticultural Society of London (R.H.S.), 2001 ($4^{th}$ edition).

Propagation:

*Method.*—Stem cuttings.

*Time to initiate roots from stem cuttings after treating cuttings with a commercial rooting hormone.*—About 2 weeks under misting and at an air temperature of 85° C.

*Rooting habit.*—Normal, branching, fleshy, and developing a thick diameter (to about 2.5 cm).

*Root color.*—Pale yellow (between RHS 161D and RHS 162D), depending on soil type.

*Crop time (under normal summer growing conditions and when grown in a 4 L container from a rooted cutting).*—8 to 10 weeks to flower with very good plant vigor.

Plant:

*Plant shape and habit.*—Hardy herbaceous perennial with 6 to 8 moderately thick upright and heavily branched main stems producing an upright spreading mound about 70 cm tall and 70 cm wide, which is widest about 30 cm above the soil line.

*Primary branches.*—8 to 16 per main stem that protrude at about a 45° angle from horizontal.

*Lateral branches.*—On the middle half of the primary stems.

*Lateral branch size.*—Between 15 cm and 30 cm long (shorter at the upper nodes) and with an average diameter of 8.0 mm at their base.

*Flower location.*—Upper ⅓ of the plant beginning at axillary nodes while still developing at the apex.

*Stem.*—Rounded, glabrous, glaucous; averages about 70 cm tall and 3.5 cm diameter at their base.

*Stem color.*—Closest to moderate yellowish green (RHS 139D).

*Internode.*—About 15 nodes per stem below flower and about 35 total, average internode length is about 3.0 cm of unpinched plant, but varies between 2.0 to 5.0 cm and are widest in lower portion of stem.

Foliage:

*Shape.*—Generally hastate, trilobed with slightly indented margins.

*Texture.*—Adaxial and abaxial matte.

*Leaf blade size.*—To about 12.0 cm long and 8.0 cm wide, larger proximally and becoming smaller in distal portion of stem.

*Foliage color.*—Adaxial and abaxial moderate yellowish green (between RHS 137D and RHS 138A).

*Veins.*—Palmate; adaxial and abaxial veins moderate yellowish green (RHS 139D).

*Petiole size (average).*—5.0 cm long and 5.0 mm wide.

*Petiole color.*—Moderate yellowish green (between RHS 137D and RHS 139D).

Flowers:

*Buds.*—One day prior to opening about 3.5 cm long and 2.5 cm in diameter, pointed apex and bluntly rounded base; and, prior to showing petals, about 3.5 cm long and 2.5 cm in diameter, ovoid with acute apex.

*Bud color.*—Exposed petal, strong red (RHS 46A); and, prior to showing petals, moderate yellowish green (RHS 139D).

*Epicalyx.*—Entire, smooth, puberulent both surfaces, linear with sharply acute apex and attenuate base, curved around sepals; typically 10 to 12 per flower; about 2.5 cm long tapering to base of about 3.0 mm wide.

*Epicalyx color.*—Adaxial and abaxial moderate yellowish green (RHS 139D).

*Sepals.*—5, proximal half connate forming campanulate star-shaped calyx; acute apex; margin entire, edentate; puberulent abaxial glabrous adaxial; individually about 3.5 cm long and about 2.5 cm wide at fusion point. From the upper side of the flower, sepals visible as a star shape in the center of the flower.

*Sepal color.*—Abaxial and adaxial color moderate yellowish green (RHS 139D).

*Flowers.*—Solitary, about 15 to 25 per main stem without pinching; primarily outwardly facing; average 23 cm across, larger in early part of flowering season; persist for one to two days, depending on temperature; effective for at least 14 weeks beginning early July and lasting into October (north Texas), no detectable fragrance.

*Petals.*—5; glabrous, slightly lustrous in the center and toward middle and perimeter, dull in the back, adnate to the androecium to form a column, imbricate to about 90% overlapping at widest part (petals about 45% overlapping the next petal to either side. Veins: Parallelly veined, veins impressed on front and ribbed on back; strong red (RHS 53B) extending from the eye zone to about the center of the petal, then fading to strong red (RHS 53C) from the center to the petal margin. Shape: Rounded. Margins: Entire, edentate, slightly frilled. Apex: Rounded. Base: Short claw-like. Surface: adaxial and abaxial glabrous, slightly ribbed. Size (average): About 11.0 cm long and about 10.5 cm wide at widest portion; center dark eye about 3.0 cm diameter. Color:

Adaxial and abaxial between strong red (RHS 53C) and deep purplish pink (RHS 55A); center eye strong red (RHS 53B).

*Gynoecium*.—Style: Enclosed in column about 5.5 cm long and 0.5 cm wide at base; column color between strong red (RHS 53C) and deep purplish pink (RHS 55A); style protruding from column and split in distal 10.0 mm portion into typically 5 branches, branch diameter 2.0 mm; branch color between strong red (RHS 53C) and deep purplish pink (RHS 55A). Stigma: Typically 5; globose, puberulose, about 3.0 mm in diameter; color nearest strong red (RHS 53C). Ovary: Superior, about 6.5 mm across at base and 6.0 mm tall; acute apex.

*Androecium*.—Filaments: Numerous, about 160; less than 1.0 mm in diameter and about 5.0 mm long; attached along nearly the entire length of column; color nearest deep purplish pink (RHS 55A). Anthers: Reniform; about 2 mm long and 1 mm wide; nearest light yellow (RHS 163D). Pollen: Numerous, globose, less than 0.1 mm long; color light yellow (RHS 163D).

*Pedicel*.—Rounded in cross section, finely puberulent; length from base of sepal to abscission point average 0.5 cm long and 4.0 mm wide.

*Pedicel color*.—Moderate yellowish green (RHS 139D).

*Peduncle*.—Rounded, puberulent, average about 3.0 cm long from abscission point to stem and 4.0 mm wide, slightly longer on earlier flowers.

*Peduncle color*.—Moderate yellowish green (RHS 139D).

*Fruit*.—Few, loculicidal capsule; glabrous; globose, occasionally with abruptly acute apex; color between light yellowish brown (RHS 199C) and dark grayish yellow (RHS 199D) when mature.

*Seed*.—Minutely floccose, typically globose; about 3.0 mm in diameter; color between dark grayish reddish brown (RHS 200A) and moderate brown (RHS 200C).

Resistance: The plant grows best with plenty of moisture, but is able to tolerate some drought once established. Other pest and disease resistance beyond that of other hardy perennial *hibiscus* cultivars has not been observed. Hardiness at least from USDA Zone 4 through 9.

Commercial use: Suitable for potted plant culture, landscaping as a specimen or en masse, and especially suited for patios and confined spaces because of the compact habit.

What is claimed is:

1. A new and distinct *Hibiscus* hybrid (L.) plant named '15334-1 GR' as shown and described herein.

* * * * *